United States Patent
Emtell et al.

(10) Patent No.: US 6,328,036 B1
(45) Date of Patent: Dec. 11, 2001

(54) ANESTHETIC APPARATUS AND METHOD FOR OPERATING SAME

(75) Inventors: Pär Emtell, Vällingby; Mikael Kock, Akersberga, both of (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/292,613

(22) Filed: Apr. 15, 1999

(30) Foreign Application Priority Data

Apr. 23, 1998 (SE) .................................................... 9801428

(51) Int. Cl.[7] .......................... A61M 16/00; A61M 16/01; A61M 16/08
(52) U.S. Cl. ................................ 128/205.14; 128/203.12; 128/203.14; 128/203.28; 128/204.28; 128/205.13; 128/205.12; 128/205.16
(58) Field of Search .......................... 128/203.12, 203.14, 128/203.28, 204.28, 205.13, 205.14, 205.12, 204.16

(56) References Cited

U.S. PATENT DOCUMENTS

| 4,127,121 | | 11/1978 | Westenkow et al. | |
|---|---|---|---|---|
| 4,972,831 | | 11/1990 | von dem Hagen et al. | |
| 5,253,640 | | 10/1993 | Falb et al. | |
| 5,509,406 | * | 4/1996 | Kock et al. | 128/203.14 |
| 5,520,172 | * | 5/1996 | Obermayer | 128/205.13 |
| 5,678,540 | * | 10/1997 | Kock et al. | 128/205.13 |
| 5,694,924 | * | 12/1997 | Cewers | 128/204.21 |
| 5,806,513 | * | 9/1998 | Tham et al. | 128/204.22 |
| 5,875,777 | * | 3/1999 | Eriksson | 128/204.21 |
| 5,957,129 | * | 9/1999 | Tham et al. | 128/204.28 |
| 6,131,571 | * | 10/2000 | Lampotang et al. | 128/204.21 |

FOREIGN PATENT DOCUMENTS

| 0 697 224 | 2/1996 | (EP) . |
|---|---|---|
| 0 745 405 | 12/1996 | (EP) . |
| 2 226 763 | 7/1990 | (GB) . |

* cited by examiner

Primary Examiner—John G. Weiss
Assistant Examiner—Mital Patel
(74) Attorney, Agent, or Firm—Schiff Hardin & Waite

(57) ABSTRACT

An anesthetic apparatus has a control unit and a breathing circuit with a connector for fresh gas, a bellows system and an outlet valve. The anesthetic apparatus operates at least as an open system, the connector then constituting an inspiratory part of the breathing circuit and the bellows system and outlet valve constituting an expiratory part of the breathing circuit. In order to reduce the adverse impact of compressible volume in the expiratory section on the functioning of the anesthetic apparatus, the control unit regulates the bellows system during inspiration so that a counter pressure, largely corresponding to the pressure of fresh gas at the connector, is maintained in the expiratory section of the breathing circuit.

5 Claims, 1 Drawing Sheet

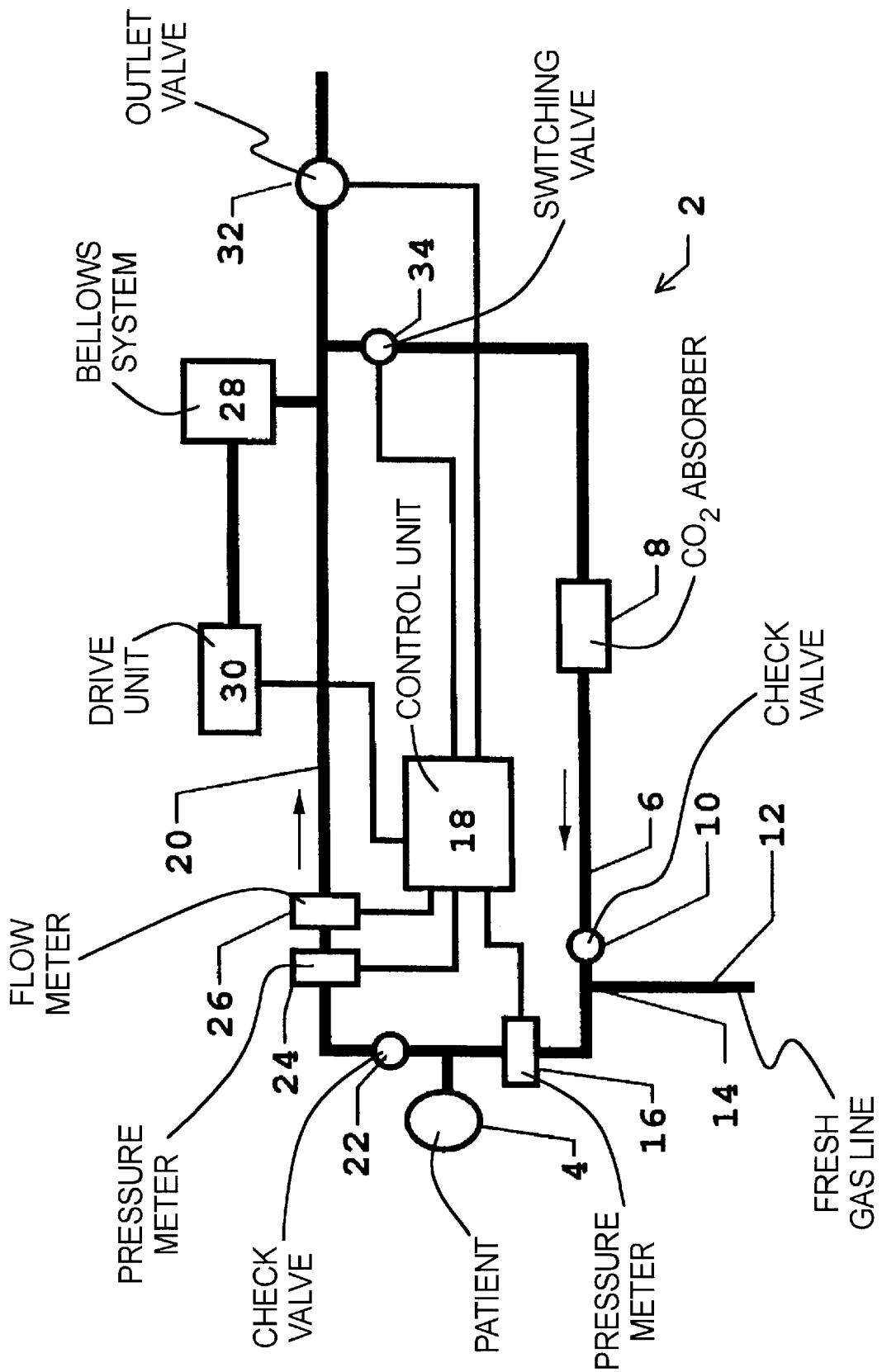

ANESTHETIC APPARATUS AND METHOD FOR OPERATING SAME

BACKGROUND OF THE INVENTION

1. Field of the Invention

The present invention is directed to an anesthetic apparatus of the type which is operable at least as an open system, wherein a connector for fresh gas is a part of an inspiratory section of a breathing circuit, and a bellows system and an outlet valve are part of an expiratory section of the breathing circuit. The present invention is also directed to a method for operating such an anesthetic apparatus.

2. Description of the Prior Art

Most anesthetic apparatuses are devised for operation in different modes, especially with open and closed systems.

In an open system, all the gas prepared in the anesthetic apparatus and delivered to the patient during inspiration (inhalation) is removed from the anesthetic apparatus and carried to an evacuation unit during expiration (exhalation).

In a closed system, a larger or smaller part of the gas expired by the patient is returned in the anesthetic apparatus to the patient at the next inspiration. Gas is usually returned to the patient via an absorber to remove carbon dioxide from the gas.

One problem with anesthetic apparatuses of this kind is that the compressible volumes in the breathing circuit are much larger than in apparatuses that cannot be switched between open and closed systems.

The large compressible volume in the expiratory section of the breathing circuit is a particular problem when the anesthetic apparatus operates as an open system. During inspiration, more than a negligible part of the programmed tidal volume may be consumed in compressible volume, since inspiratory pressure is greater than expiratory pressure.

SUMMARY OF THE INVENTION

An object of the present invention is to provide an anesthetic apparatus with which the aforementioned problems are eliminated.

Another object of the present invention is to provide a method for operating an anesthetic apparatus that eliminates the aforementioned problems.

The above object is achieved is accordance with the invention in an anesthetic apparatus having a control unit and a breathing circuit with a connector for fresh gas, a bellows system and an outlet valve, the anesthetic apparatus being operable at least as an open system wherein the connector is a part of an inspiratory section of the breathing circuit and the bellows system and the outlet valve are a part of an expiratory section of the breathing circuit, and wherein the control unit regulates the bellows system during inspiration so that a counter-pressure, substantially corresponding to the pressure of the fresh gas at the connector, is maintained in the expiratory section of the breathing circuit.

The bellows system in the expiratory section of the breathing circuit is, in conventional systems, disconnected in functional respects when the anesthetic apparatus operates as an open system. By instead, in the inventive method and apparatus, making active use of the presence of the bellows system and controlling the bellows system (and possibly even the outlet valve) by a control unit to supply gas to the expiratory section of the breathing circuit during inspiration, a counter-pressure can be built up in this section. None of the fresh gas supplied to the breathing circuit's inspiratory section will then be consumed by compressible volume.

DESCRIPTION OF THE DRAWINGS

The single FIGURE is a schematic block diagram of an anesthetic apparatus constructed and operating in accordance with the present invention.

DESCRIPTION OF THE PREFERRED EMBODIMENTS

The FIGURE shows the basic components of one embodiment of the anesthetic apparatus according to the invention. A breathing circuit 2 is connected to a patient 4 to carry gas to and from the patient 4. Gas lines are depicted with broad lines and electrical lines with lines of normal thickness.

The breathing circuit 2 has an inspiratory section 6 in which a carbon dioxide absorber 8 is arranged. The absorber 8 is shown mainly to indicate that the breathing circuit 2 is also suitable for closed systems. A first check valve 10 is arranged to keep gas from flowing from the patient 4 into the inspiratory section 6. A fresh gas line 12 is connected to a connector 14 in the inspiratory section 6 to supply fresh breathing gas (containing an anesthetic) to the patient 4. A first pressure meter 16 measures pressure in the inspiratory section 6.

The value measured for pressure is supplied to a control unit 18 which controls the various components and units in the anesthetic apparatus (also see below).

The breathing circuit 2 also has an expiratory section 20 in which a second check valve 22 is arranged to prevent expired gas from flowing back to the patient 4. A second pressure meter 24 and a flow meter 26 are also arranged in the expiratory section 20. A bellows system 28 which, in a closed system, forces breathing gas through the breathing circuit 2, is connected to the expiratory section 20. The bellows system 28 is operated by a drive unit 30.

An outlet valve 32 is arranged at the end of the expiratory section 20 and regulates the discharge of gas into an evacuation unit (not shown).

The FIGURE also shows a switching valve 34 for switching between an open system and a closed system.

Compressible volume in the expiratory section 20 is relatively large, i.e. several liters. In a conventional system, this means that 20 to 50 ml of breathing gas are required to build up pressure in the expiratory section 20 during inspiration. Since open systems are primarily used in conjunction with small tidal volumes, i.e. from 100 to 300 ml per breath, a not inconsiderable part of the tidal volume is lost.

Compensation for this loss can indeed be made by the addition of extra fresh gas, but this would increase total gas losses considerably and simultaneously impose a delay before the patient 4 receives any gas.

An anesthetic apparatus according to the invention eliminates the problems in another way.

When an inspiration commences by a flow of fresh gas from the fresh gas line 12, the bellows system 28 is simultaneously activated by the control unit 18. The control unit 18 controls the bellows system 28 according to the gas pressure measured, so the same pressure builds up in the inspiratory section 6 and the expiratory section 20. Minimal compressible volume then persists, and it only causes losses measured in milliliters. The patient 4 therefore receives the entire tidal volume without any needless gas losses in the system.

Regulation based on the signal from the flow meter 26 can be used as an alternative to regulation based on pressure values determined by the pressure meters 16, 24. The bellows system is then regulated so flow through the flow meter 26 is zero or close to zero. A zero flow means that pressure in the expiratory section 20 is at least equal to pressure in the inspiratory section 6. Pressure in the expiratory section 20, however, should not greatly exceed pressure in the inspiratory section 6. If a small flow is allowed, gas losses would indeed increase somewhat, but pressure in the expiratory section 20 would not exceed pressure in the inspiratory section 6.

When the actual volumes in the breathing system 2 and the flow and pressure of supplied fresh gas are known, the control unit 18 even can have the bellows system 18 generate an appropriate counter flow/counter pressure without feedback from the values measured in the system.

The outlet valve 32 can also be used during inspiration for achieving rapid compliance with the desired pressure/flow.

It should be noted that the bellows system can consist of any suitable pressure-generating unit, e.g. a pump, piston, fan or compressor. It is advantageous for the bellows system 28 to rapidly supply or take up gas, enabling it to respond rapidly to changes in the system.

Although modifications and changes may be suggested by those skilled in the art, it is the intention of the inventors to embody within the patent warranted hereon all changes and modifications as reasonably and properly come within the scope of their contribution to the art.

We claim as our invention:

1. An anesthetic apparatus operable at least as an open system, comprising:
    a breathing circuit having an expiratory section and an inspiratory section;
    a connector for fresh gas;
    a bellows system;
    an outlet valve;
    said connector being a part of said inspiratory section during operation as an open system and said bellows system and said outlet valve being a part of said expiratory section during operation as an open system; and
    a control unit connected to said bellows system for operating said bellows system to maintain, during inspiration, a counter-pressure in said expiratory section substantially corresponding to a pressure of fresh gas at said connector.

2. An anesthetic apparatus as claimed in claim 1 further comprising a first pressure meter disposed at said connector and a second pressure meter disposed in said expiratory section, said first and second pressure meter supplying respective output signals to said control unit and said control unit regulating said bellows system dependent on said output signals.

3. An anesthetic apparatus as claimed in claim 1 further comprising a flow meter disposed in said expiratory section which emits an output signal dependent on flow in said expiratory section, said output signal being supplied to said control unit and said control unit regulating said bellows system dependent on said output signal.

4. An anesthetic apparatus as claimed in claim 1 wherein said control unit also regulates said outlet valve during inspiration to maintain said counter-pressure.

5. A method for operating an anesthetic apparatus as an open system comprising the steps of:
    measuring an inspiratory pressure in an inspiratory section of an anesthetic apparatus; and
    generating a counter-pressure in said expiratory section substantially equal to said inspiratory pressure to reduce an impact of compressible volume on said expiratory section during inspiration.

* * * * *